(12) United States Patent
Bohlin et al.

(10) Patent No.: US 7,265,124 B2
(45) Date of Patent: Sep. 4, 2007

(54) CRISTALLINE AND AMORPHOUS FORM OF A TRIAZOLO (4,5-D) PYRIDIMINE COMPOUND

(75) Inventors: Martin Bohlin, Södertälje (SE); Steve Cosgrove, Loughborough (GB); Bo Lassen, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 39 days.

(21) Appl. No.: 11/240,801

(22) Filed: Oct. 3, 2005

(65) Prior Publication Data

US 2007/0173518 A1    Jul. 26, 2007

Related U.S. Application Data

(63) Continuation of application No. 10/296,990, filed as application No. PCT/SE01/01239 on May 31, 2001, now abandoned.

(30) Foreign Application Priority Data

Jun. 2, 2000    (GB)    ................. 0013407.2

(51) Int. Cl.
C07D 487/04    (2006.01)
A61K 31/519    (2006.01)
A61P 7/02    (2006.01)
A61P 9/10    (2006.01)

(52) U.S. Cl. .................................. 514/261.1; 544/254
(58) Field of Classification Search .................. None
See application file for complete search history.

(56) References Cited

U.S. PATENT DOCUMENTS

| 6,525,060 B1 | 2/2003 | Hardern et al. ........... 514/261.1 |
| 6,713,483 B1 | 3/2004 | Guile et al. ............... 514/261.1 |
| 2003/0148888 A1 | 8/2003 | Larsson et al. ............. 544/254 |
| 2006/0025590 A1* | 2/2006 | Hardern et al. ........... 514/261.1 |

FOREIGN PATENT DOCUMENTS

| WO | 9905143 | 2/1999 |
| WO | 0034283 | 6/2000 |

* cited by examiner

*Primary Examiner*—Mark L. Berch
(74) *Attorney, Agent, or Firm*—Nixon & Vanderhye

(57) ABSTRACT

The invention provides new forms of a chemical compound of formula (I). The invention relates to forms of a chemical compound (I), in particular to crystalline and amorphous forms, more particularly four crystalline forms and an amorphous form. The invention further relates to processes for the preparation of such forms, to pharmaceutical compositions comprising the compound in crystalline and/or amorphous form and to therapeutic use of such forms.

31 Claims, 6 Drawing Sheets

*Figure 1.1 Polymorph 1*

*Figure 1.2 Polymorph II*

Figure 1.3 Polymorph III

Figure 1.4 Polymorph III

Figure 1.5 Form α with some Polymorph II

Figure 2

CRISTALLINE AND AMORPHOUS FORM OF A TRIAZOLO (4,5-D) PYRIDIMINE COMPOUND

This application is a CON of 10/296,990 Dec. 2, 2002 ABN which is a 371 of PCT/SE01/01239 filed May 31, 2001.

The present invention relates to forms of a chemical compound, in particular to crystalline and amorphous forms, more particularly four crystalline forms and an amorphous form. The invention further relates to processes for the preparation of such forms, to pharmaceutical compositions comprising the compound in crystalline and/or amorphous form and to the therapeutic use of such forms.

In the formulation of drug compositions, it is important for the drug substance to be in a form in which it can be conveniently handled and processed. This is of importance, not only from the point of view of obtaining a commercially viable manufacturing process, but also from the point of subsequent manufacture of pharmaceutical formulation comprising the active compound. Chemical stability, solid state stability, and shelf life of the active ingredients are also very important factors. The drug substance, and compositions containing it, should be capable of being effectively stored over appreciable periods of time, without exhibiting a significant change in the active component's physicochemical characteristics (e.g. its chemical composition, density, hygroscopicity and solubility). Moreover, it is also important to be able to provide drug in a form which is as pure as possible. Amorphous materials may present significant problems in this regard. For example, such materials are typically more difficult to handle and to formulate than crystalline material, provide for unreliable solubility, and are often found to be unstable and chemically impure. The skilled person will appreciate that, if a drug can be readily obtained in a stable crystalline form, the above problems may be solved. Thus, in the manufacture of commercially viable and pharmaceutically acceptable, drug compositions, it is desirable, wherever possible, to provide drug in a substantially crystalline, and stable, form. It is to be noted, however, that this goal is not always achievable. Indeed, typically, it is not possible to predict, from molecular structure alone, what the crystallisation behaviour of a compound will be, and this can usually only be determined empirically.

Platelet adhesion and aggregation are initiating events in arterial thrombosis. Although the process of platelet adhesion to the sub-endothelial surface may have an important role to play in the repair of damaged vessel walls, the platelet aggregation that this initiates can precipitate acute thrombotic occlusion of vital vascular beds, leading to events with high morbidity such as myocardial infarction and unstable angina. The success of interventions used to prevent or alleviate these condition, such as thrombolysis and angioplasty are also compromised by platelet-mediated occlusion or re-occlusion.

It has been found that adenosine-5'-diphosphate (ADP) acts as a key mediator of thrombosis. ADP-induced platelet aggregation is mediated by the $P_{2T}$ receptor subtype located on the platelet membrane. The $P_{2T}$ receptor (also known as $P2Y_{ADP}$ or $P2T_{AC}$) is primarily involved in mediating platelet aggregation/activation and is a G-protein coupled receptor which is as yet uncloned. The pharmacological characteristics of this receptor have been described, for example, in the references by Humphries et al., *Br. J. Pharmacology* (1994), 113, 1057-1063, and Fagura et al., *Br. J. Pharmacology* (1998) 124, 157-164. Recently it has been shown that antagonists at this receptor offer significant improvements over other anti-thrombotic agents (see *J. Med. Chem.* (1999) 42, 213). International Patent Application WO 9905143 discloses generically a series of triazolo[4,5-d]pyrimidine compounds having activity as $P_{2T}$ ($P2Y_{ADP}$ or $P2T_{AC}$) antagonists. The compound of formula (I) (as depicted below) is embraced by the generic scope of International Patent Application WO 9905143 but is not specifically disclosed therein. This compound exhibits high potency as a $P_{2T}$ ($P2Y_{ADP}$ or $P2T_{AC}$) antagonist. It also has a surprisingly high metabolic stability and bioavailability.

Accordingly the present invention relates to the compound of formula (I):

(I)

in a substantially crystalline form.

The compound of formula (I) is conventionally named: {1S-[1α, 2α, 3β(1S*,2R*),5β]}-3-(7-{[2-3,4-difluorophenyl)cyclopropyl]amino}-5-(propylthio)-3H-1,2,3-triazolo[4,5-d]pyrimidin-3-yl)-5-(2-hydroxyethoxy)cyclopentane-1,2-diol.

The compound of formula (I) may exist in four different substantially crystalline forms referred to hereafter as Polymorph I, Polymorph II, Polymorph III and Polymorph IV. A polymorph is a particular crystalline form of a compound.

The different physical properties of polymorphic forms with respect to each other and with respect to the amorphous state may influence markedly the chemical and pharmaceutical processing of a compound, particularly when the compound is prepared or used on an industrial scale.

In one aspect of the invention, the preferred crystalline form of the compound of formula (I) is in the form of Polymorph I, Polymorph II, Polymorph III and/or Polymorph IV.

In an alternative aspect of the invention, a preferred crystalline form of the compound of formula (I) is Polymorph I.

In another aspect of the invention, a preferred crystalline form of the compound of formula (I) is Polymorph II.

In a further aspect of the invention, a preferred crystalline form of the compound of formula (I) is Polymorph III.

In an additional aspect of the invention, a preferred crystalline form of the compound of formula (I) is Polymorph IV.

In a further aspect of the invention, the compound of formula (I) is in a substantially amorphous form. In an amorphous form, the three dimensional long range order that normally exists in a crystalline form (for example in a polymorph) does not exist, and the positions of the molecules relative to one another in the amorphous form are essentially random (see B. C. Hancock and g. Zografi, J. Pharm. Sci. (1997) 86 1). The amorphous form of the compound of formula (I) is referred to as Form α.

We have isolated the compound of formula (I) in crystalline and amorphous forms. These forms may exist substantially or essentially free of water ("anhydrous" forms). Therefore in one aspect of the invention there is provided an anhydrous form of the compound of formula (I) in a crystalline form or an amorphous form. By the use of the term "substantially pure and essentially in the anhydrous form", we doe not exclude the presence of some solvent, including water, within the crystal lattice structure or outside the crystal lattice structure. An anhydrous form has less than 0.4 water molecules per compound molecule (less than 40% hydrated). Preferably, the anhydrous form contains less than 0.1 water molecules per compound molecule.

Polymorphs I, II, III and IV can be distinguished by reference to their onset of melting, powder X-ray diffraction patterns and/or single crystal X-ray data.

Polymorph I has an onset of melting which is in the range 146-152° C., for example about 151° C., when it is substantially pure and essentially in the anhydrous form.

Polymorph II has an onset of melting that is in the range 136-139° C., for example about 137.5° C., when it is substantially pure and essentially in the anhydrous form.

Polymorph III has an onset of melting that is in the range 127-132° C., for example about 132° C., when it is substantially pure and essentially in the anhydrous form.

Polymorph IV has an onset of melting which is typically about 139° C., when it is substantially pure and essentially in the anhydrous form.

Form α typically undergoes a glass transition followed by crystallisation into one of the above Polymorph forms, for example Polymorph II, prior to melting.

The melting points were determined using differential scanning calorimetry (DSC) using Perkin Elmer DSC7 instrumentation. The onset of melting is defined as the point at which a significant change from the baseline occurs and was measured by Perkin Elmer Pyris software. It will be appreciated that alternative readings of melting point may be given by other types of equipment or by using conditions different to those described here. Hence the figures quoted are not to be taken as absolute values. The skilled person will realise that the precise value of the melting point will be influenced by the purity of the compound, the sample weight, the heating rate and the particle size.

Polymorph I, when it is substantially pure and essentially in the anhydrous form, has an X-ray powder diffraction pattern containing specific peaks of high intensity at 5.3° (±0.1°), 20.1° (±0.1°), 20.7° (±0.1°) 21.0° (±0.1°) and 21.3° (±0.1°) 2θ. More preferably, substantially pure and essentially anhydrous Polymorph I has an X-ray powder diffraction pattern containing specific peaks at 5.3°(±0.1°), 8.0° (±0.1°), 9.6° (±0.1°), 13.9° (±0.1°), 15.3° (±0.1°), 20.1° (±0.1°), 20.7° (±0.1°), 21.0° (±0.1°), 21.3° (±0.1°), 26.2° (±0.1°) and 27.5° (±0.1°) 2θ.

Polymorph II, when it is substantially pure and essentially in the anhydrous form, has an X-ray powder diffraction pattern containing specific peaks of high intensity at 5.5° (±0.1°), 13.5° (±0.1°), 18.3° (±0.1°), 22.7° (±0.1°) and 24.3° (±0.1°) 2θ. More preferably, substantially pure and essentially anhydrous Polymorph II has an X-ray powder diffraction pattern containing specific peaks at 5.5° (±0.1°), 6.8° (±0.1°), 10.6° (±0.1°), 13.5° (±0.1°), 14.9° (±0.1°), 18.3° (±0.1°), 19.2° (±0.1°), 22.7° (±0.1°), 24.3° (±0.1°) and 27.1° (±0.1°) 2 θ.

Polymorph III, when it is substantially pure and essentially in the anhydrous form, has an X-ray powder diffraction pattern containing specific peaks of high intensity at 14.0° (±0.1°), 17.4° (±0.1°), 18.4° (±0.1°), 21.4° (±0.1°) and 24.1° (±0.1°) 2θ. More preferably, substantially pure and essentially anhydrous Polymorph III has an X-ray powder diffraction pattern containing specific peaks at 5.6° (±0.1°), 12.5° (±0.1°), 14.0° (±0.1°), 17.4° (±0.1°), 18.4° (±0.1°), 21.4° (±0.1°), 22.2° (±0.1°), 22.9° (±0.1°), 24.1° (±0.1°) and 24.5° (±0.1°) 2θ.

Polymorph IV, when it is substantially pure and essentially in the anhydrous form, has an X-ray powder diffraction pattern containing specific peaks of high intensity at 4.9° (±0.1°), 9.2° (±0.1°), 11.6° (±0.1°), 15.6° (±0.1°) and 16.4° (±0.1°) 2θ. More preferably, substantially pure and essentially anhydrous Polymorph IV has an X-ray powder diffraction pattern containing specific peaks at 4.9° (±0.1°), 6.0° (±0.1°), 9.2° (±0.1°), 11.6° (±0.1°), 12.8° (±0.1°), 15.6° (±0.1°), 16.4° (±0.1°), 17.2° (±0.1°) and 18.1° (±0.1°) 2θ.

Form α, when it is substantially pure and essentially in the anhydrous form, has an X-ray powder diffraction pattern containing no sharp peaks.

The X-ray data for Polymorph II, Polymorph III, Polymorph IV and Form α were obtained using Siemens D5000 equipment. The X-ray diffraction data for Polymorph I was obtained using a Philips X'Pert MPD machine. It will be appreciated that different equipment and/or conditions may result in slightly different data being generated. Hence the figures quoted are not to be taken as absolute values.

In an alternative aspect of the invention, a solvated form may be formed, for example, a hydrated form (a "hydrate"). Therefore in this aspect of the invention there is provided a hydrate of the compound of formula (I) in crystalline form. A hydrate has 0.8 or more water molecules per compound molecule (80% or more hydrated). A hemi-hydrate has between 0.4 and 0.8 water molecules per compound molecule (40-80% hydrated).

In a further feature of the invention there is provided any mixture of crystalline and/or amorphous forms of the compound of formula (I). Preferably, the mixture is of Polymorph I, Polymorph II, Polymorph III, Polymorph IV and/or Form α. More preferably, the invention provides any mixture of Polymorph II and Polymorph III.

In a further feature of the invention there is provided a process for the production of a crystalline form of the compound of formula (I) by crystallisation of the compound of formula (I) from a suitable solvent. Preferably the solvent is selected from the group: ethanol, ethyl acetate, iso-propanol, iso-octane, acetonitrile, water, or a mixture thereof. More preferably, the solvent is selected from the group: ethanol, ethyl acetate, iso-prapanol, iso-octane, water, or a mixture thereof. Suitably, the solvent is selected from the group: a mixture of methanol and water, ethanol, ethyl acetate, a mixture of ethanol and water, a mixture of iso-prapanol and water, a mixture of ethyl acetate and iso-octane, and acetonitrile.

The compound of formula (I) can be prepared by methods analogous to those described in WO 9905143.

To initiate crystallisation, seeding with crystal(s) or the compound of formula (I) may be required. Seeding with the required polymorph may be necessary to obtain the polymorph of choice. Crystallisation of the compound of formula (I) from an appropriate solvent system may be achieved by attaining supersaturation, for example, by cooling, by solvent evaporation and or by the addition of an anti-solvent (a solvent in which the compound of formula (I) is poorly soluble; examples of suitable anti-solvents include heptane or isooctane). Crystallisation temperatures and times will vary depending upon the concentration of the compound in solution, the solvent system used and the method of crystallisation adopted.

The compound of formula (I) in crystalline form may be isolated from the above reaction mix using techniques well known to those skilled in the art, for example, by decanting, filtration or centrifuging. Similarly the compound of formula (I) in crystalline form may be dried in accordance with well-known procedures.

Optional recrystallisation step(s) may be performed using the same or different solvent systems to reduce further impurities, such as amorphous material, chemical impurities or to convert the crystalline form from one polymorph into another polymorph or into a hydrate or an anhydrous form. In addition a conditioning step may be performed, exposing the solid to high humidity, in order to remove amorphous material.

Preferably the crystallisation is carried out directly from the reaction solution. Alternatively the crystallisation is performed from a subsequent solution.

In a further feature of the invention, there is provided a process for preparing Polymorph I, which comprises obtaining a few seed crystals of Polymorph I from the slow crystal growth of Polymorph I from a melt of Polymorph II, and using this to seed a reaction mixture comprising of the compound of formula (I), and a suitable mixed solvent system such as methanol/water.

In a further feature of the invention, there is provided a process for preparing Polymorph II, which comprises crystallisation in a suitable solvent such as ethyl acetate.

In a further feature of the invention, there is provided a process for preparing Polymorph III, which comprises crystallisation in a suitable solvent such as an alcohol, for example ethanol or isopropyl alcohol (IPA), in particular seeding with crystals or Polymorph III or slurrying a compound of formula (I) in a suitable solvent such as IPA.

In a further feature of the invention, there is provided a process for preparing Polymorph IV, which comprises crystallisation from a suitable solvent such as acetonitrile, in particular seeding with crystals of Polymorph IV or a period of slurrying a compound of formula (I) in a suitable solvent such as acetonitrile.

A further feature of the invention provides a process for preparing Polymorph III substantially free of Polymorph II, which comprises, for example, slurrying a compound of formula (I) in $C_{1-6}$ aliphatic alcohol/water solvent system (preferably IPA/water) at a temperature of 5-65° C. for 1-10 days.

In a further feature of the invention, there is provided a process for the production of the compound of formula (I) in substantially amorphous form which comprises freeze drying or spray drying a solution of a compound of Formula (I) using a suitable solvent system, for example ethanol/water.

The term "substantially free" refers to less than 10% of the other polymorph, preferably less than 5%.

In a further aspect of the invention, there is provided a compound obtainable by any of the above-mentioned processes.

The compound of formula (I) in crystalline and/or amorphous form acts as $P_{2T}(P2Y_{ADP}$ or $P2T_{AC})$ receptor antagonists. Accordingly, the compound of formula (I) in crystalline and/or amorphous forms is useful in therapy, including combination therapy. In particular, the compound of formula (I) in crystalline form is indicated for use in the treatment or prophylaxis of arterial thrombotic complications in patients with coronary artery, cerebrovascular or peripheral vascular disease. Arterial thrombotic complications may include unstable angina, primary arterial thrombotic complications of atherosclerosis such as thrombotic or embolic stroke, transient ischaemic attacks, peripheral vascular disease, myocardial infarction with or without thrombolysis, arterial complications due to interventions in atherosclerotic disease such as angioplasty, including coronary angioplasty (PTCA), endarterectomy, stent placement, coronary and other vascular graft surgery, thrombotic complications of surgical or mechanical damage such as tissue salvage following accidental or surgical trauma, reconstructive surgery including skin and muscle flaps, conditions with a diffuse thrombotic/platelet consumption component such as disseminated intravascular coagulation, thrombotic thrombocytopaenic purpura, haemolytic uraemic syndrome, thrombotic complications of septicaemia, adult respiratory distress syndrome, anti-phospholipid syndrome, heparin-induced thrombocytopaenia and pre-eclampsia/eclampsia, or venous thrombosis such as deep vein thrombosis, venocclusive disease, haematological conditions such as myeloproliferative disease, including thrombocythaemia, sickle cell disease; or in the prevention of mechanically-induced platelet activities in vivo, such as cardio-pulmonary bypass and extracorporeal membrane oxygenation (prevention of microthromboembolism), mechanically-induced platelet activation in vitro, such as use in the preservation of blood products, e.g. platelet concentrates, or shunt occlusion such as in renal dialysis and plasmapheresis, thrombosis secondary to vascular damage/inflammation such as vasculitis, arteritis, glomerulonephritis, inflammatory bowel disease and organ graft rejection, conditions such as migraine, Raynaud's phenomenon, conditions in which platelets can contribute to the underlying inflammatory disease process in the vascular wall such as atheromatous plaque formation/progression, stenosis/restenosis and in other inflammatory conditions such as asthma, in which platelets and platelet-derived factors are implicated in the immunological disease process. Further indications include treatment of CNS disorders and prevention of the growth and spread of tumours.

According to a further aspect of the present invention there is provided a compound of formula (I) in crystalline and/or amorphous form for use in a method of treatment of the human or animal body by therapy.

According to an additional feature of the present invention there is provided the compound of formula (I) in crystalline and/or amorphous form for use as a medicament. Preferably, the compound of formula (I) in crystalline and/or amorphous form is used as a medicament to antagonise the $P_{2T}(P2Y_{ADP}$ or $P2T_{AC})$ receptor in a warm-blooded animal such as a human being. More preferably, the compound of formula (I) in crystalline and/or amorphous form is used as a medicament for treating or preventing arterial thrombotic complications in patients with coronary artery, cerebrovascular or peripheral vascular disease in a warm-blooded animal such as a human being.

According to the invention there is further provided the use of the compound of formula (I) in crystalline and/or amorphous form in the manufacture of a medicament for use as an antagonist of the $P_{2T}(P2Y_{ADP}$ or $P2T_{AC})$ receptor. In particular there is further provided the use of the compound of formula (I) in crystalline and/or amorphous form in the manufacture of a medicament for use in the treatment or prevention of arterial thrombotic complications in patients with coronary artery, cerebrovascular or peripheral vascular disease.

The invention also provides a method of treatment or prevention of arterial thrombotic complications in patients with coronary artery, cerebrovascular or peripheral vascular disease, which comprises administering to a person suffering from or susceptible to such a disorder a therapeutically effective amount of the compound of formula (I) in crystalline and/or amorphous form.

The compound of formula (I) in crystalline and/or amorphous form may be administered topically, e.g. to the lung and/or the airways, in the form of solutions, suspensions, HFA aerosols and dry powder formulations; or systemically, e.g. by oral administration in the form of tablets, pills, capsules, syrups, powders or granules, or by parenteral administration in the form of sterile parenteral solutions or suspensions, by subcutaneous administration, or by rectal administration in the form of suppositories or transdermally.

The compound of formula (I) in crystalline and/or amorphous form may be administered on its own or as a pharmaceutical composition comprising the compound of formula (I) in crystalline and/or amorphous form in combination with a pharmaceutically acceptable diluent, adjuvant and/or carrier. Therefore there is provided as a further feature of the invention a pharmaceutical composition comprising the compound of formula (I) in crystalline and/or amorphous form in association with a pharmaceutically acceptable diluent, adjuvant and/or carrier. Particularly preferred are compositions not containing material capable of causing an adverse reaction, such as an adverse allergic reaction.

Dry powder formulations and pressurized HFA aerosols of the compound of formula (I) in crystalline and/or amorphous form may be administered by oral or nasal inhalation. For inhalation the compound of formula (I) in crystalline and/or amorphous form is desirably finely divided. The compound of formula (I) in crystalline and/or amorphous form may also be administered by means of a dry powder inhaler. The inhaler may be a single or a multi dose inhaler, and may be a breath actuated dry powder inhaler.

One possibility is to mix the finely divided compound of formula (I) in crystalline and/or amorphous form with a carrier substance, e.g. a mono-, di- or polysaccharide, a sugar alcohol or another polyol. Suitable carriers include sugars and starch. Alternatively the finely divided compound of formula (I) in crystalline and/or amorphous form may be coated by another substance. The powder mixture may also be dispensed into hard gelatine capsules, each containing the desired dose of the active compound of formula (I) in crystalline and/or amorphous form.

Another possibility is to process the finely divided powder into spheres which break up during the inhalation procedure. This spheronized powder may be filled into the drug reservoir of a multidose inhaler, e.g. that known as the Tubuhaler® in which a dosing unit meters the desired dose which is then inhaled by the patient. With this system the active compound of formula (I) with or without a carrier substance is delivered to the patient. The pharmaceutical composition comprising the compound of formula (I) in crystalline and/or amorphous form may conveniently be tablets, pills, capsules, syrups, powders or granules for oral administration; sterile parenteral or subcutaneous solutions, suspensions for parenteral administration or suppositories for rectal administration.

For oral administration the compound of formula (I) in crystalline and/or amorphous form may be admixed with an adjuvant or a carrier, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol, waxes, paraffin, and the like, and then compressed into tablets. If coated tablets required, the cores, prepared as described above, may be coated with a concentrated sugar solution which may contain e.g. gum arabic, gelatine, talcum, titanium dioxide, and the like. Alternatively, the tablet may be coated with a suitable polymer dissolved either in a readily volatile organic solvent or an aqueous solvent.

For the preparation of soft gelatine capsules, the compound of formula (I) in crystalline and/or amorphous form may be admixed with e.g. a vegetable oil or polyethylene glycol. Hard gelatine capsules may contain granules of the compound using either the above mentioned excipients for tablets, e.g. lactose, saccharose, sorbitol, mannitol, starches, cellulose derivatives or gelatine. Also liquid or semisolid formulation of the drug may be filled into hard gelatine capsules.

Liquid preparations for oral application may be in the form of syrups or suspensions, for example solutions containing the compound of formula (I) in crystalline and/or amorphous form, the balance being sugar and a mixture of ethanol, water, glycerol and propylene glycol. Optionally such liquid preparations may contain colouring agents, flavouring agents, saccharine and carboxymethylcellulose as a thickening agent or other excipients known to those skilled in art.

FIG. 1.1 is an X-ray diffraction pattern for Polymorph I was obtained using a Philips X'Pert MPD machine in θ-θ configuration over the scan range 1° to 40° 2θ with 2 or 5 seconds exposure per 0.02° 2θ increment. The X-rays were generated by a copper long-fine focus tube operated at 40 kV and 50 mA. The wavelength of the X-rays was 1.5406 Å.

FIG. 1.2 is an X-ray diffraction pattern for Polymorph II obtained using a Siemens D5000 machine in θ-θ configuration over the scan range 2° to 30° 2θ with 4 seconds exposure per 0.02° 2θ increment. The X-rays were generated by a copper long-fine focus tube operated at 45 kV and 40 mA. The wavelength of the X-rays was 1.5406 Å. Data were collected using a zero background on which ~10 mg of the compound was placed. The holder was made from a single crystal of silicon, which had been cut along a non-diffracting plane and then polished to an optically flat finish. The X-rays incident upon this surface were negated by Bragg extinction.

FIG. 1.3 is an X-ray diffraction pattern for Polymorphs III obtained using a Siemens D5000 machine as described above.

FIG. 1.4 is an X-ray diffraction pattern for Polymorphs IV obtained using a Siemens D5000 machine as described above.

FIG. 1.5 is an X-ray diffraction pattern for Form α obtained using a Siemens D5000 machine as described above.

FIG. 2 shows DSC graphs for Polymorph I, II, III and IV and Form α obtained using a Perkin Elmer DSC 7 instrument. The pan type was aluminum with a pierced lid. The sample weight was 1 to 3 mg. The procedure was carried out under a flow of nitrogen gas (30 ml/min) and the temperature range studied was 30° C. to 325° C. at a constant rate of temperature increase of 10° C. per minute.

Figure 2:
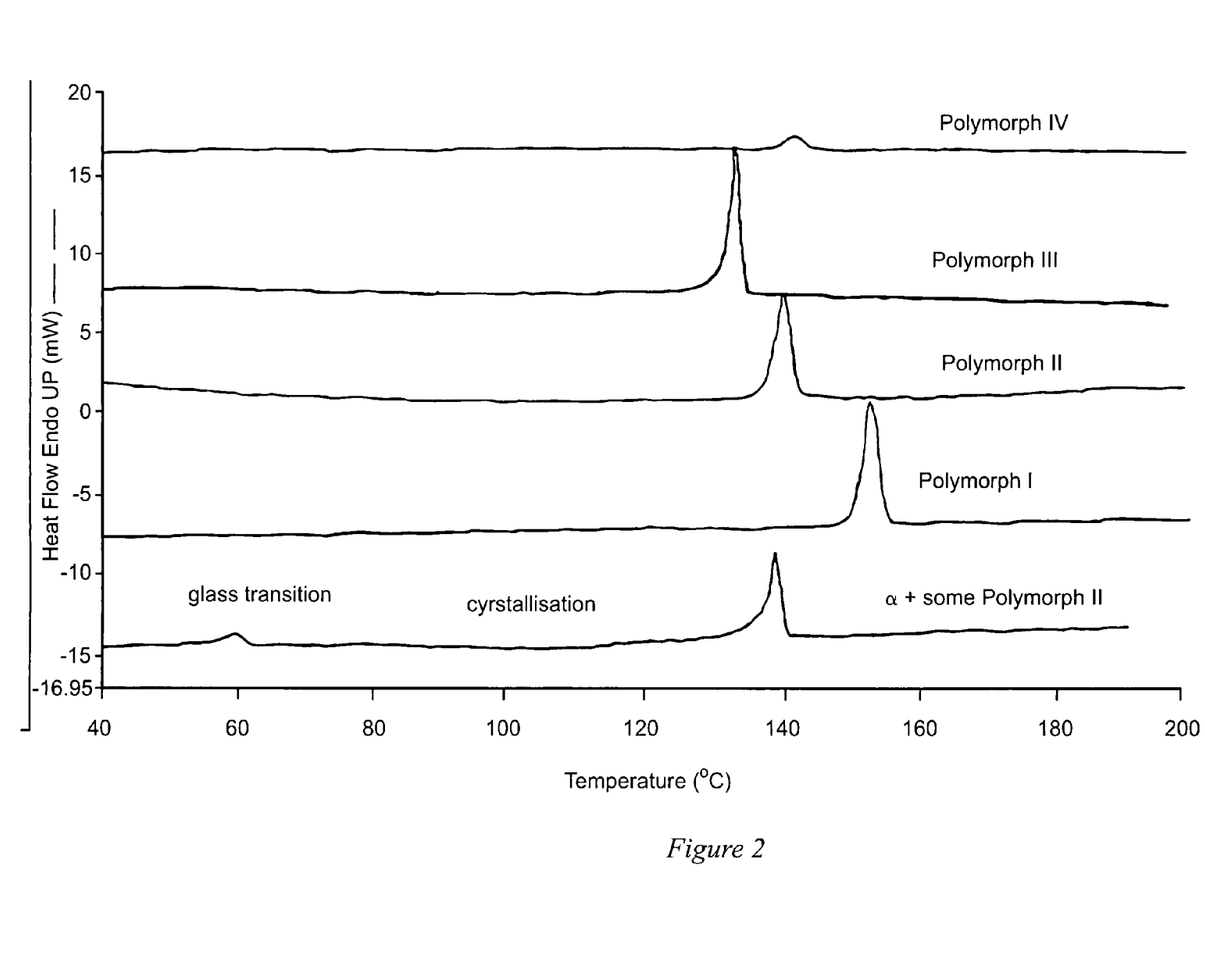
Figure 11:
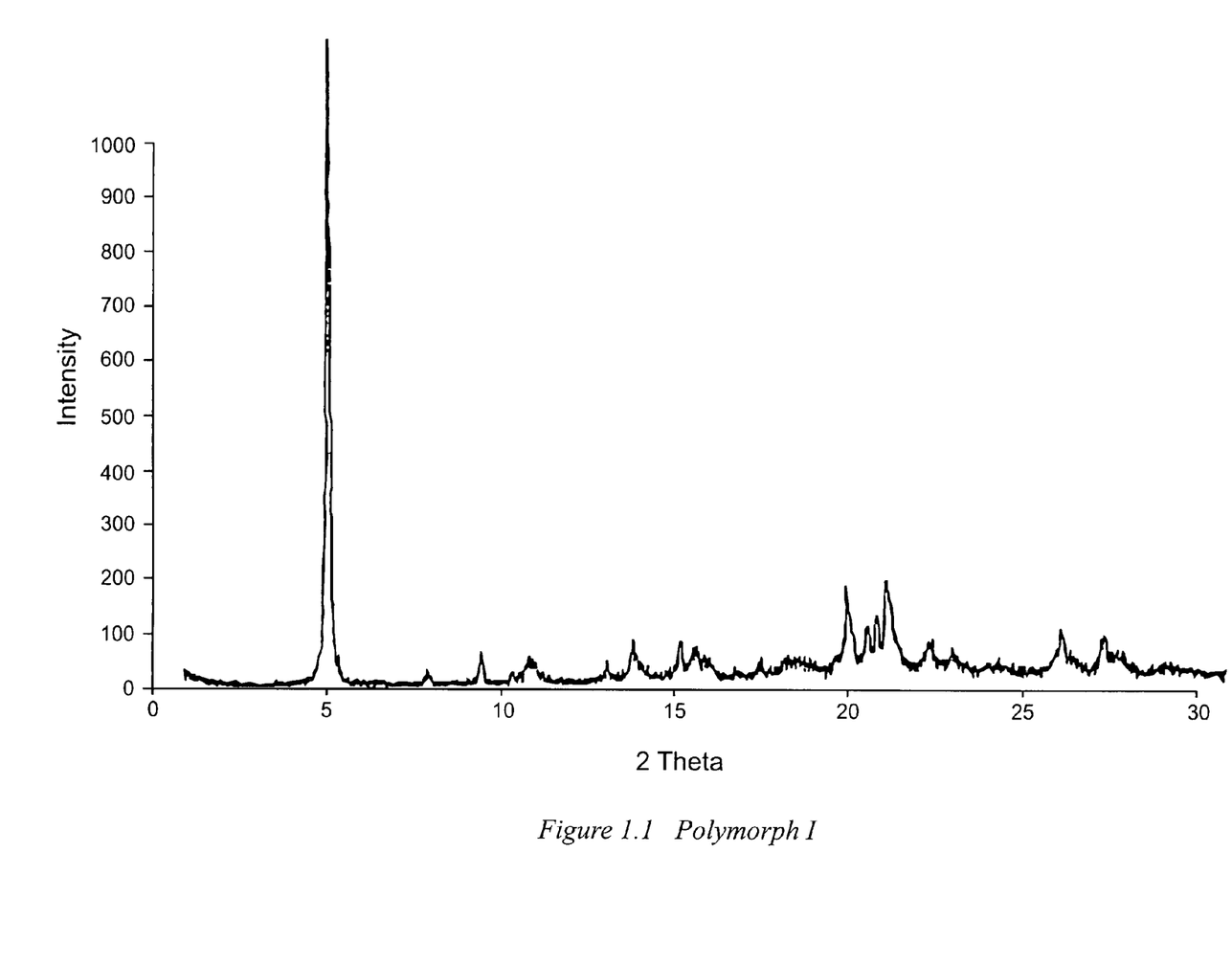
Figure 12:
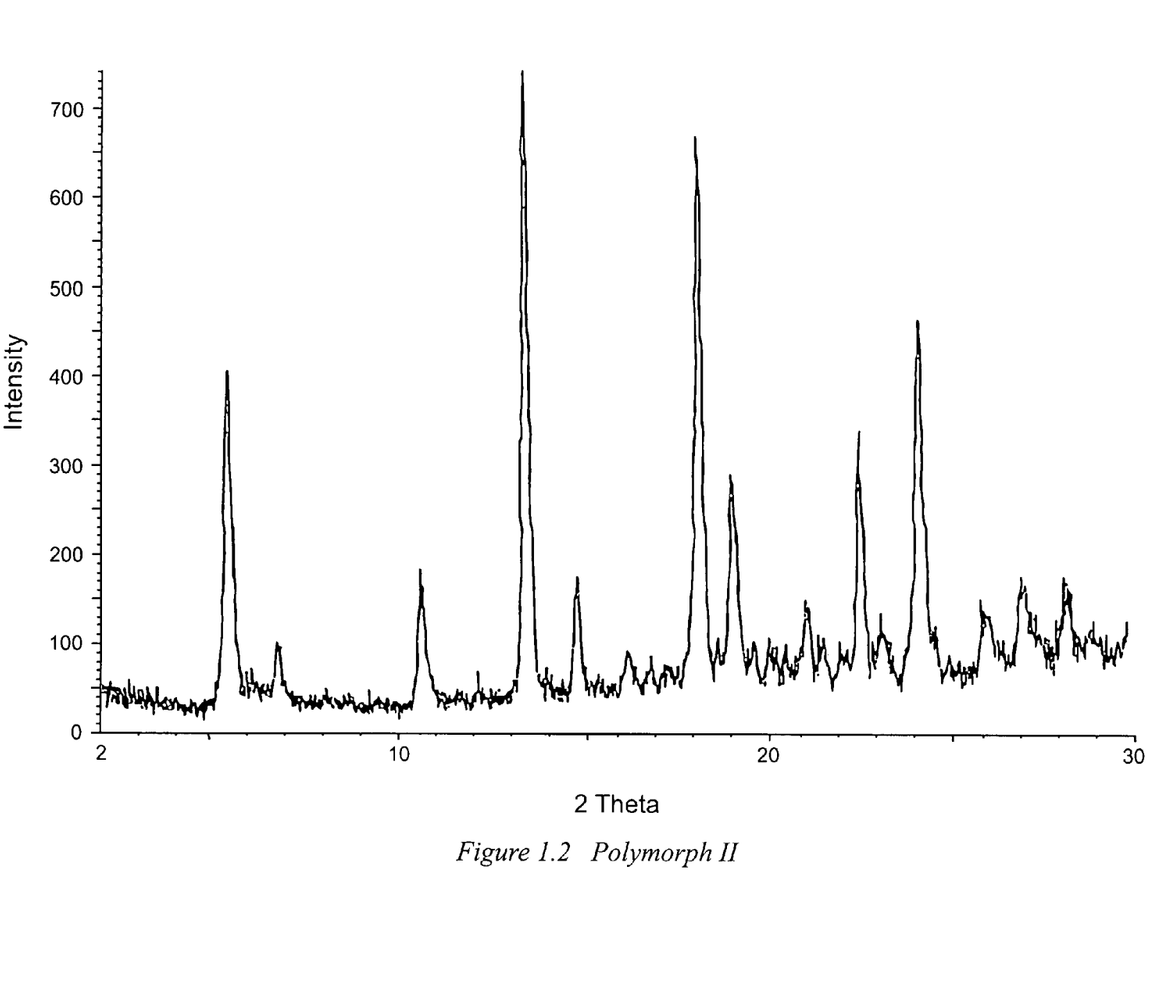
Figure 13:
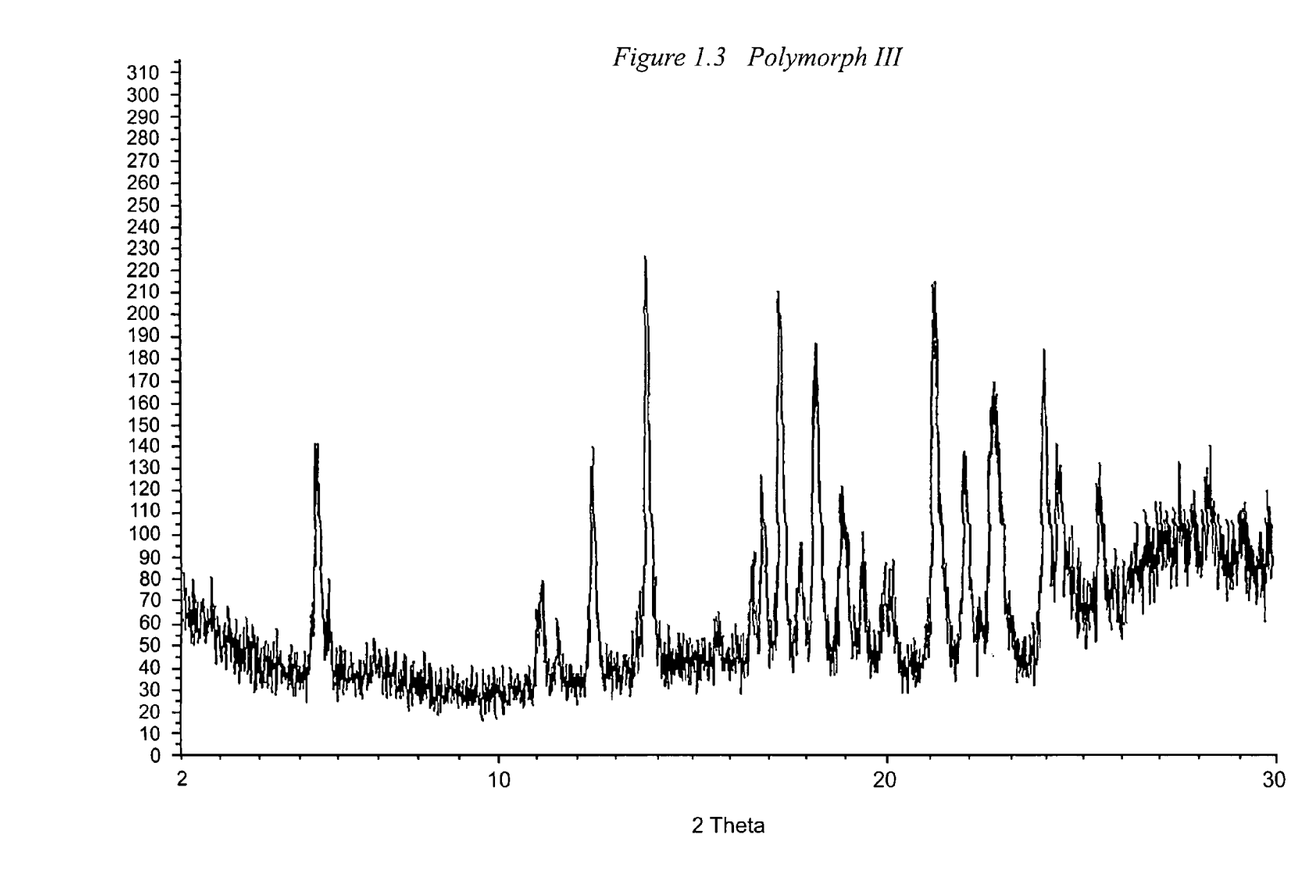
Figure 14:
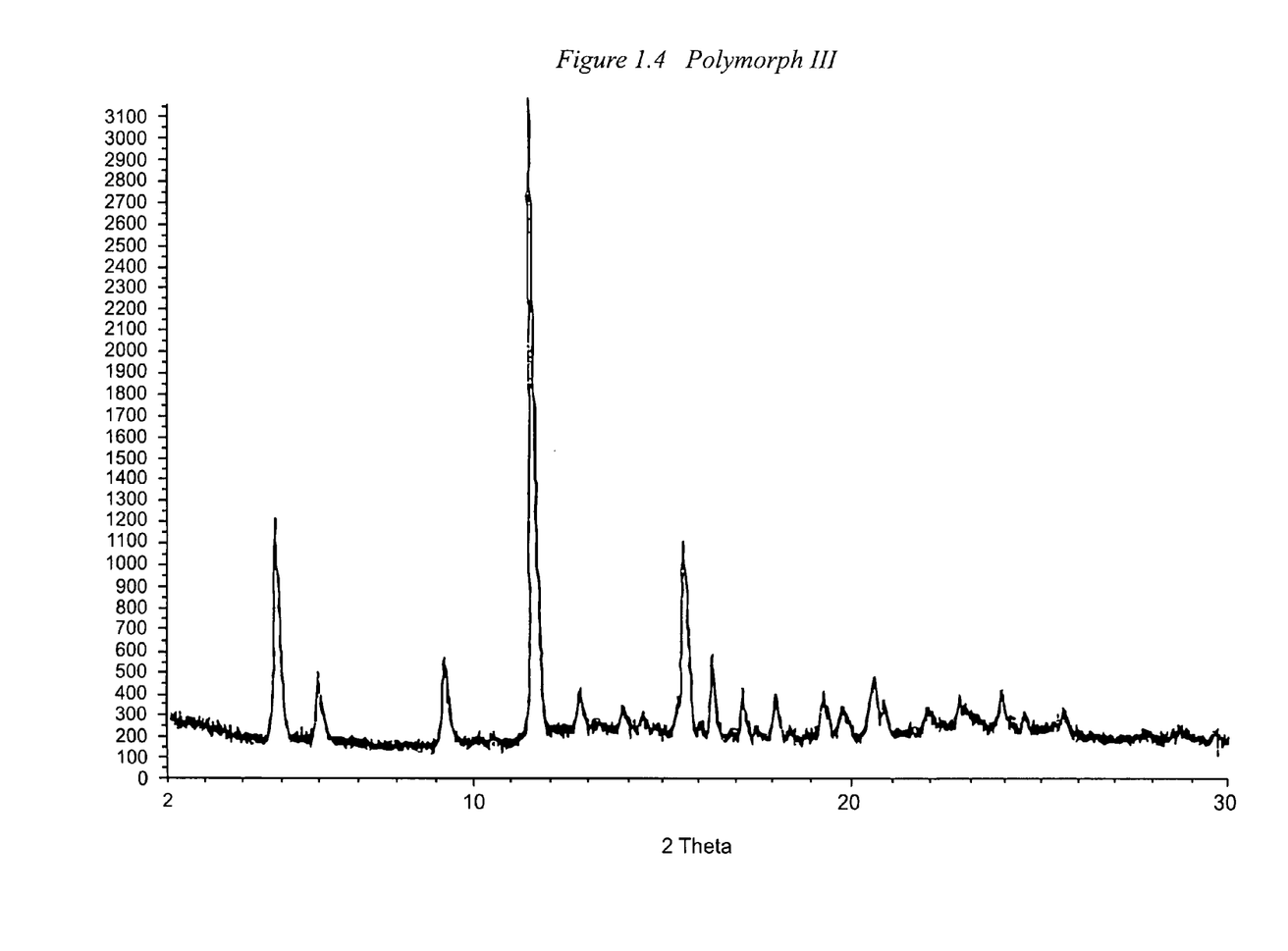
Figure 15:
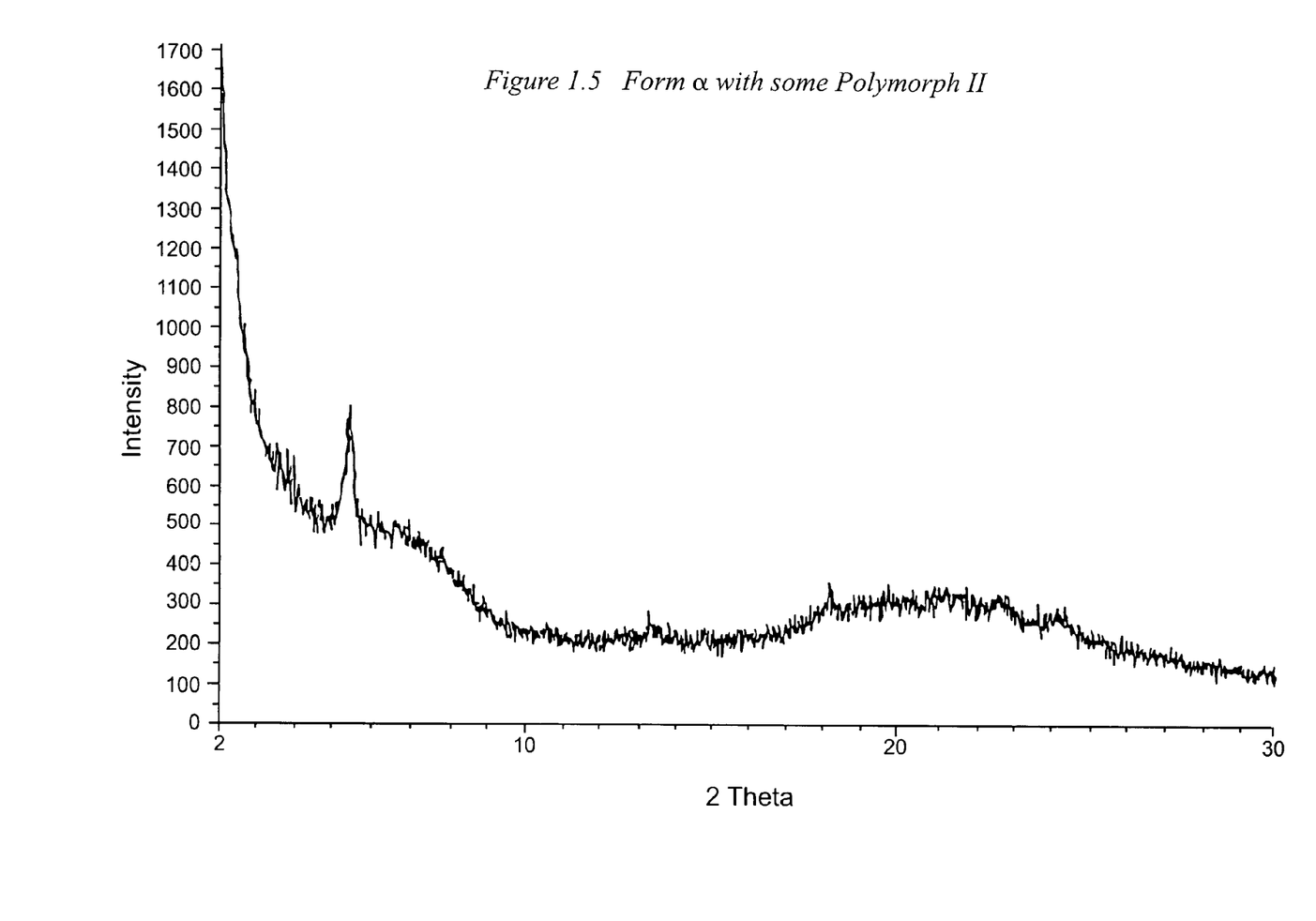

It should be realised that analysis of samples with grains above 30 microns in size and non-unitary aspect ratios may affect the relative intensity of peaks. The skilled person will also realise that the position of reflections is affected by the precise height at which the sample sits in the diffractometer and the zero calibration of the diffractometer. The surface planarity of the sample may also have a small effect. Hence the diffraction pattern data presented are not to be taken as absolute values.

The invention may be illustrated in the following non-limiting Examples.

EXAMPLE 1

{1S-[1α, 2α, 3β(1S*,2R*),5β]}-3-(7-{[2-3,4-difluorophenyl)cyclopropyl]amino}-5-(propylthio)-3H-1,2,3-triazolo[4,5-d]pyrimidin-3-yl)-5-(2-hydroxyethoxy)cyclopentane-1,2-diol in the form of Polymorph I.

Part 1

The compound of formula (I) in the form of Polymorph II (2 mg) was heated and cooled in a DSC in the following way: 35 to 143 to 35 to 148 to 35 to 148 to 35° C. This annealing process resulted in the crystallisation of pure Polymorph I as indicated by DSC.

Part 2

A solution comprising of the compound of formula (I) 5 ml/g methanol and 7.3 ml/g water and a small quantity of seeds of Polymorph I, was crystallised at 30° C. XRPD and DSC confirmed that substantially pure Polymorph I had been formed.

EXAMPLE 2

{1S-[1α,2α,3β(1S*,2R*),5β]}-3-(7-{[2-(3,4-difluorophenyl)cyclopropyl]amino}-5-(propylthio)-3H-1,2,3-triazolo[4,5-d]pyrimidin-3-yl)-5-(2-hydroxyethoxy)cyclopentane-1,2-diol in the form of Polymorph II.

Chloroform (150 μl) was added to 45 mg of the compound of formula (I) and the mixture was warmed to dissolution over a steam bath. The resulting solution was left to crystallise over night and dried under flowing nitrogen. XRPD and DSC confirmed that substantially pure Polymorph II had been formed.

EXAMPLE 3

{1S-[1α,2α,3β(1S*,2R*),5β]}-3-(7-{[2-(3,4-difluorophenyl)cyclopropyl]amino}-5-(propylthio)-3H-1,2,3-triazolo[4,5-d]pyrimidin-3-yl)-5-(2-hydroxyethoxy)cyclopentane-1,2-diol in the form of Polymorph III Ethanol (200 μl) was added to 10 mg of the compound of formula (I) and the mixture warmed to dissolution over a steam bath. The resulting solution was left to crystallise over night. XRPD and DSC confirmed that a mixture of Polymorphs II and III had been formed. This material was used to seed a larger scale preparation: 191 mg of Polymorph II were slurried in 1 ml of 50% aqueous solution of isopropanol. To this slurry, 15 mg of seeds of mixed Polymorph II/III were added. After 2 days complete conversion into Polymorph III had occurred as shown by XRPD.

EXAMPLE 4

{1S-[1α,2α,3β(1S*,2R*),5β]}-3-(7-{[2-(3,4-difluorophenyl)cyclopropyl]amino}-5-(propylthio)-3H-1,2,3-triazolo[4,5-d]pyrimidin-3-yl)-5-(2-hydroxyethoxy)cyclopentane-1,2-diol in the form of Polymorph IV Acetonitrile (0.12 ml) was added to 10 mg of the compound of formula (I) and the mixture warmed to dissolution over a steam bath. The warm solution was allowed to cool slowly in a warm jacket of hot water. The resulting crystals were dried under nitrogen. XRPD indicated that this was a distinct polymorph.

EXAMPLE 5

{1S-[1α,2α,3β(1S*,2R*),5β]}-3-(7-{[2-(3,4-difluorophenyl)cyclopropyl]amino}-5-(propylthio)-3H-1,2,3-triazolo[4,5-d]pyrimidin-3-yl)-5-(2-hydroxyethoxy)cyclopentane-1,2-diol predominantly in the form of Form α.

The compound of formula (I) (218 mg) was dissolved in a 50% aqueous solution of ethanol (24 ml). To this solution, a further 14.5 ml of water were added dropwise. The resulting saturated solution was then freeze dried using Virtis instrumentation under the following conditions (vacuum 2170 mT, run time 20.2 hours, condensed temperature −52° C., ambient temperature 20.3° C.).

REFERENCE EXAMPLE 1

{1S-[1α,2α,3β(1S*,2R*),5β]}-3-(7-{[2-(3,4-difluorophenyl)cyclopropyl]amino}-5-(propylthio)-3H-1,2,3-triazolo[4,5-d]pyrimidin-3-yl)-5-(2-hydroxyethoxy)cyclopentane-1,2-diol A solution of {3aR-[3aα,4α,6α(1R*,2S*),6aα]}-2-[6-({7-[2-(3,4-difluorophenyl) cyclopropyl]amino-5-(propylthio)-3H-1,2,3-triazolo[4,5-d]pyrimidin-3-yl}tetrahydro-2,2-dimethyl-4H-cyclopenta-1,3-dioxol-4-yl)oxy]ethanol (Method A, 0.59 g) in trfluoroacetic acid (15 ml) and water (15 ml) was stirred at room temperature for 30 minutes. The reaction mixture was carefully added to a solution of sodium bicarbonate (21 g) in water (150 ml) and stirred for 30 minutes. The mixture was extracted with ethyl acetate, which was dried and evaporated. The residue was purified (SiO$_2$, ethyl acetate as eluent) to afford the title compound (0.44 g), MS (APCI) 523 (M+H$^+$, 100%); NMR: 8.95 (1 H, d, J=3.3), 7.39–7.21 (2 H, m), 7.10–7.00 (1 H, m), 5.12 (1 H, d, J=6.4), 5.05 (1 H, d, J=3.6), 4.96 (1 H, q, J=9.0), 4.62–4.54 (2 H, m), 3.95 (1 H, br s), 3.79–3.73 (1 H, m), 3.55–3.47 (4 H, m), 3.20–3.13 (1 H, m), 2.98–2.81 (2 H, m), 2.63 (1 H, dt, J=13 6, 8.5), 2.29–2.21 and 2.16–2.09 (1 H, m) 2.07–2.00 (1 H,m), 1.73–1.33 (4 H, m), 0.99 (3 H, t, J=7.4).

PREPARATION OF STARTING MATERIALS

The starting materials are either commercially available or are readily prepared by standard methods from known materials. For example the following reactions are illustrations but not limitations of the preparation of some of the starting materials used in the above reactions.

Method A

{3aR-[3aα,4α,6α(1R*,2S*),6aα]}-2-[6-({7-[2-(3,4-Difluorophenyl) cyclopropyl]amino-5-(propylthio)-3H-1,2,3-triazolo[4,5-d]pyrimidin-3-yl}tetrahydro-2,2-dimethyl-4H-cyclopenta-1,3-dioxol-4-yl)oxy]ethanol DIBAL-H®(1.0 M solution in hexanes, 5.15 ml) was added to an ice-cooled solution of {3aR-[3aα,4α, 6α(1R*,2S*),6aα]}-{[6-(7-{[2-(3,4-Difluorophenyl)cyclopropyl]amino}-5-(propylthio)-3H-1,2,3-triazolo[4,5-d]-pyrimidin-3-yl)-tetrahydro-2,2-dimethyl-4H-cyclopenta-1,3-dioxol-4-yl]oxy} acetic acid, methyl ester (Method B, 0.76 g) in THF (1 ml) and the solution was stirred at this temperature for 2 hours. The reaction mixture was concentrated in vacuo and the residue was dissolved in ethyl acetate (75 ml). A saturated aqueous solution of sodium potassium tartrate (75 ml) was added and the mixture stirred vigorously for 16 hours. The organics were collected and the aqueous re-extracted with ethyl acetate (2×50 ml). The combined organics were dried and concentrated and the residue purified (SiO$_2$, isohexane:ethylacetate 1:1 as eluant) to give the title compound (0.63 g). MS (APCI) 563 (M+H$^+$,100%).

Method B

{3aR-[3aα, 4α,6α(1R*,2S*),6aα]}-{[6-(7-{[2-(3,4-Difluorophenyl)cyclopropyl]amino}-5-(propylthio)-3H-1,2,3-triazolo[4,5-d]-pyrimidin-3-yl)-tetrahydro-2,2-dimethyl-4H-cyclopenta-1,3-dioxol-4-yl]oxy} acetic acid, methyl ester To a mixture of [3aR-(3aα,4α,6α,6aα)]-({6-[7-bromo-5-(propylthio)-3H-1,2,3-triazolo[4,5-d]-pyrimidin-3-yl]-tetrahydro-2,2-dimethyl-4H-cyclopenta-1,3-dioxol-4-ol}oxy) acetic acid, methyl ester (Method D, 0.80 g) and (1R-trans)-2-(3,4-difluorophenyl) cyclopropanamine,[R-(R*,R*)]-2,3-dihydroxybutanedioate (1:1) (Method C, 0.61 g) in dichloromethane (25 ml) was added N,N-diisopropylethylamine (0.85 ml). The resulting solution was stirred at room temperature for 16 hours then concentrated in vacuo. Purification (SiO$_2$, isohexane:ethylacetate 3:1 as eluant) gave the title compound as a colourless foam (0.77 g). MS (APCI) 591 (M+H$^+$, 100%).

Method C (1R-trans)-2-(3,4-Difluorophenyl)cyclopropanamine,[R-(R*,R*)]-2,3-dihydroxybutanedioate (1:1)

The title compound may be prepared according to the procedure described in WO 9905143.

Method D

[3aR-(3aα,4α,6α,6aα)]-({6-[7-Bromo-5-(propylthio)-3H-1,2,3-triazolo[4,5-d]-pyrimidin-3-yl]-tetrahydro-2,2-dimethyl-4H-cyclopenta-1,3-dioxol-4-ol}oxy)acetic acid, methyl ester [3aR-(3aα,4α,6α,6aα)]-({6-[7-Amino-5-(propylthio)-3H-1,2,3-triazolo[4,5-d]-pyrimidin-3-yl]-tetrahydro-2,2-dimethyl-4H-cyclopenta-1,3-dioxol-4-ol}oxy)acetic acid, methyl ester (Method E, 1.1 g) and isoamylnitrite (2.4 ml) in bromoform (30 ml) was heated at 80° C. for 30 minutes. The cooled reaction mixture was purified (SiO$_2$, ethyl acetate:isohexane 1:4 as eluant) to afford the title compound (0.44 g), MS (APCI) 502/4 (M+H$^+$), 504 (100%).

Method E

[3aR-(3aα,4α,6α,6aα)]-({6-[7-Amino-5-(propylthio)-3H-1,2,3-triazolo[4,5-d]-pyrimidin-3-yl]-tetrahydro-2,2-dimethyl-4H-cyclopenta-1,3-dioxol-4-ol}oxy)acetic acid, methyl ester To a solution of [3aR-(3aR-(3aα,4α,6α,6aα)]-6-[7-Amino-5-(propylthio)-3H-1,2,3-triazolo[4,5-d]-pyrimidin-3-yl]-tetrahydro-2,2-dimethyl-4H-cyclopenta-1,3-dioxol-4-ol (Method F, 0.50 g) in THF (25 ml) at 0° C., was added butyllithium (0.62 ml of 2.5 N in hexanes). After 20 minutes, the suspension was treated with solution of trifluoromethanesulfonyloxy-acetic acid methyl ester (0.34 g) (prepared according to the method of Biton, Tetrahedron, 1995, 51, 10513) in THF (10 ml). The resulting solution was allowed to warm to room temperature then concentrated and purified (SiO$_2$, ethyl acetate:hexane 4:6 as eluant) to afford the title compound (0.25 g), MS (APCI) 439 (M+H$^+$, 100%).

Method F

[3aR-(3aα,4α,6α,6aα)]-6-[7-Amino-5-(propylthio)-3H-1,2,3-triazolo[4,5-d]-pyrimidin-3-yl]-tetrahydro-2,2-dimethyl-4H-cyclopenta-1,3-dioxol-4-ol

[3aR-(3aα,4α,6α,6aα)-6-[7-Chloro-5-(propylthio)-3H-1,2,3-triazolo[4,5-d]-pyrimidin-3-yl]-tetrahydro-2,2-dimethyl-4H-cyclopenta-1,3-dioxol-4-ol (Method G, 13.2 g) in THF (200 ml) containing 0.88 ammonia (5 ml ) was stirred for 2 hours then concentrated to dryness and the residue partitioned between water and ethyl acetate. The organics were dried and then concentrated to afford the title compound (12.5 g). MS (APCI) 367 (M+H$^+$, 100%)

Method G

[3aR-(3aα,4α,6α,6aα)]-6-[7-Chloro-5-(propylthio)-3H-1,2,3-triazolo[4,5-d]-pyrimidin-3-yl]-tetrahydro-2,2-dimethyl-4H-cyclopenta-1,3-dioxol-4-ol Isoamyl nitrite (1.1 ml) was added to a solution of [3aR-(3aα,4α,6α,6aα)]-6-{[5-amino-6-Chloro-2-(propylthio)pyrimidin-4-yl]amino}-tetrahydro-2,2-dimethyl-4H-cyclopenta-1,3-dioxol-4-ol (Method H, 2.0 g) in acetonitrile (100 ml) and the solution was heated at 70° C. for 1 hour. The cooled reaction mixture was concentrated and purified (SiO$_2$, ethyl acetate:isohexane 1:3 as eluant) to afford the title compound (1.9 g).MS (APCI) 386 (M+H$^+$, 100%).

Method H

[3aR-(3aα,4α,6α,6aα)]-6-{[5-Amino-6-Chloro-2-(propylthio)pyrimidin-4-yl]amino}-tetrahydro-2,2-dimethyl-4H-cyclopenta-1,3-dioxol-4-ol Iron powder (3.0 g) was added to a stirred solution of [3aR-(3aα,α,6α,6aα)]-6-{[6-chloro-5-nitrol-2-(propylthio)pyrimidin-4-yl]amino}tetrahydro-2,2-dimethyl-4H-cyclopenta-1,3-dioxol-4-ol (Method I, 2.7 g) in acetic acid (100 ml). The reaction mixture was stirred at room temperature for 2 hours, concentrated to half volume, diluted with ethyl acetate and washed with water. The organic phase was dried and concentrated to afford the title compound (2.0 g). MS (APCI) 375 (M+H$^+$,100%).

Method I

[3aR-(3aα,4α,6α,6aα)]-6-{[6-Chloro-5-nitro-2-(propylthio)pyrimidin-4-yl]amino}tetrahydro-2,2-dimethyl-4H-cyclopenta-1,3-dioxol-4-ol A solution of [3aR-(3aα,4α,6α,6aα)-6-aminotetrahydro-2,2-dimethyl-4H-cyclopenta-1,3-dioxol-4-ol, hydrochloride (Method J, 10.0 g) and N,N-diisopropylethylamine (35 ml) in THF (600 ml) was stirred for 1 hour. The mixture was filtered and the solution was added over 1 hour to a solution of 4,6-dichloro-5-nitro-2-(propylthio)pyrimidine (WO 9703084, 25.6 g) in THF (1000 ml) and stirred for a further 2 hours. The solvent volume was reduced in vacuo and ethyl acetate was added (1000 ml). The mixture was washed with water and the organic layers were dried, evaporated and purified (SiO$_2$, isohexane-ethyl acetate as eluant) to afford the title compound (14.2 g). MS (APCI) 405 (M+H$^+$,100%).

Method J

[3aR-(3aα,4α,6α,6aα)]-6-Aminotetrahydro-2,2-dimethyl-4H-cyclopenta-1,3-dioxol-4-ol, hydrochloride

[1R-(1α,2β,3β,4α)]-2,3,4-Trihydroxycyclopentenylimidodicarbonic acid, bis(1,1-dimethylethyl) ester (Method K, 17.4 g) in 6 M HCl (100 ml)/methanol (500 ml) was stirred for 18 hours. The mixture was evaporated and then azeotroped with toluene (4×200 ml) to give a colourless powder (8.7 g). This solid was suspended in acetone (250 ml) containing 2,2-dimethoxypropane (25 ml) and cone. HCl (0.2 ml) then heated under reflux for 2 hours. The mixture was cooled, evaporated and azeotroped with toluene (3×200 ml). The residue was dissolved in 20% aqueous acetic acid and stirred for 2 hours. The mixture was evaporated and azeotroped with toluene (4×200 ml) to afford the title compound (10.1 g). MS (APCI) 174 (M+H$^+$,100%).

Method K

[1R-(1α,2β,3β,4α)]-2,3,4-Trihydroxycyclopentenylimidodicarbonic acid, bis(1,1-dimethylethyl) ester To a solution of (1R-cis)-Bis(1,1-dimethylethyl)-4-hydroxy-2-cyclopentenylimidio-dicarbonate (Method L, 17.1 g) in THF (500 ml)/water (50 ml) added N-methylmorpholine-N-oxide (9.4 g) followed by osmium tetroxide (10 ml, 2.5% solution t-butanol). The mixture was stirred at room temperature for 4 days then treated with sodium hydrosulphite (6.0 g). The suspension was filtered through diatomaceous earth and the product purified (SiO$_2$, ethyl acetate:hexane 1:1 as eluant) to afford the title compound (19.1 g). NMR: 144 (18 H, s), 1.46-160 (1 H, m), 1.97-2.05 (1 H, m), 3.55-3.58 (1 H, m), 3.66-3.73 (1 H, m), 4.11-4.21 (2 H, m), 4.54 (1 H, d, J=4.8), 4.56 (1 H, d, J=5.9), 4.82 (1 H, d, J=4.6).

Method L (1R-cis)-Bis(1,1-dimethylethyl)-4-hydroxy-2-cyclopentenylimidodicarbonate To a suspension of ether washed sodium hydride (60% dispersion in oil; 0.31 g) in THF (30 ml) was added imidodicarbonic acid bis-(1,1-dimethylethyl)ester (1.84 g). The mixture was stirred at 40° C. for 1 hour. To the mixture, at ambient temperature, was then added (1S-cis)-4-acetoxy-2-cyclopenten-1-ol (0.5 g) and tetrakis(triphenylphosphine) palladium(0) (0.18 g). The reaction mixture was stirred for 24 hours then purified (SiO$_2$, ethyl acetate:hexane 1:9 as eluant) to give the title compound as a colourless solid (0.90 g). NMR: 1.43 (18 H, s), 1.61 (1 H, ddd, J=12,3, 7.7, 6.4), 2.54 (1 H, dt, J=12.6, 7.4), 4.51-4.57 (1 H, m), 4.86 (1 H, tq, J=8.0, 1.8) 4.91 (1 H, d, J=5.4), 5.71-5.77 (2 H, m).

EXAMPLE 2

The following illustrate representative pharmaceutical dosage forms containing the compound formula (I) in crystalline and/or amorphous form (hereafter compound X), for therapeutic or prophylactic use in humans:

| (a) Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 |
| Lactose Ph.Eur | 488.5 |
| Magnesium stearate | 1.5 |

| (e) Injection I | (50 mg/ml) |
|---|---|
| Compound X | 5.0% w/v |
| 1N Sodium hydroxide solution | 15.0% w/v |
| 0.1N Hydrochloric acid | (to adjust pH to 7.6) |
| Polyethylene glycol 400 | 4.5% w/v |
| Water for injection to 100% | |

| (f) Injection II | (10 mg/ml) |
|---|---|
| Compound X | 1.0% w/v |
| Sodium phosphate BP | 3.6% w/v |
| 0.1N Sodium hydroxide solution | 15.0% w/v |
| Water for Injection to 100% | |

| (g) Injection III | (1 mg/ml, buffered to pH 6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

Note
The above formulations may be obtained by conventional procedures well known in the pharmaceutical art. The tablets (a)-(c) may be enteric coated by conventional means, for example to provide a coating of cellulose acetate phthalate.

NMR spectra were measured on a Varian Unity Inova 300 or 400 spectrometer, NMR data is quoted in the form of delta values for major diagnostic protons, given in parts per million (ppm) relative to tetramethylsilane (TMS) as an internal standard using perdeuterio dimethyl sulphoxide (DMSO-$\delta_6$) as solvent unless otherwise indicated; for examples which showed the presence of rotamers in the proton NMR spectra only the chemical shifts of the major rotamer are quoted; coupling constants (J) are given in Hz.

Mass Spectra (MS) were measured as follows: EI spectra were obtained on a VG 70-250S or Finnigan Mat Incos-XL spectrometer, FAB spectra were obtained on a VG70-250SEQ spectrometer, ESI and APCI spectra were obtained on Finnigan Mat SSQ7000 or a Micromass Platform spectrometer.

Preparative HPLC separations were generally performed using a Novapak®, Bondapak® or Hypersil® column packed with BDSC-18 reverse phase silica.

Flash chromatography (indicated in the Examples as (SiO$_2$)) was carried out using Fisher Matrix silica, 35-70 μm.

| Abbreviations | |
|---|---|
| THF | tetrahydrofuran |
| XRPD | X-ray Powder Diffraction |
| DSC | Differential scanning calorimetry |

The invention claimed is:

1. A compound of formula (I):

selected from:

a compound of formula (I) characterised by an X-ray powder diffraction pattern containing specific peaks of high intensity at 5.3° (±0.1°), 20.1° (±0.1°), 20.7° (±0.1°), 21.0° (±0.1°) and 21.3° (±0.1°) 2θ;

a compound of formula (I) characterised by an X-ray powder diffraction pattern containing specific peaks of high intensity at 5.5° (±0.1°), 13.5° (±0.1°), 18.3° (±0.1°), 22.7° (±0.1°) and 24.3° (±0.1°) 2θ;

a compound of formula (I) characterised by an X-ray powder diffraction pattern containing specific peaks of high intensity at 14.0° (±0.1°), 17.4° (±0.1°), 18.4° (±0.1°), 21.4° (±0.1°) and 24.1° (±0.1°) 2θ; and a compound of formula (I) characterised by an X-ray powder diffraction pattern containing specific peaks of high intensity at 4.9° (±0.1°), 9.2° (±0.1°), 11.6° (±0.1°), 15.6° (±0.1°) and 16.4° (±0.1°) 2θ.

2. A compound of formula (I) as claimed in claim 1 that exists in an anhydrous form.

3. A compound of formula (I) as claimed in claim 1 characterised by an X-ray powder diffraction pattern containing specific peaks at 5.3° (±0.1°), 8.0° (±0.1°), 9.6° (±0.1°), 13.9° (±0.1°), 15.3° (±0.1°), 20.1° (±0.1°), 20.7° (±0.1°), 21.0° (0.1°), 21.3° (±0.1°), 26.2° (±0.1°) and 27.5° (±0.1°) 2θ.

4. A compound of formula (I) as claimed in claim 1 characterised by a differential scanning calorimetry curve to have an onset of melting which is in the range 146-152° C.

5. A compound of formula (I) as claimed in claim 1 characterised by an X-ray powder diffraction pattern containing specific peaks at 5.5° (±0.1°), 6.8° (±0.1°), 10.6° (±0.1°), 13.5° (±0.1°), 14.9° (±0.1°), 18.3° (±0.1°), 19.2° (±0.1°), 22.7° (±0.1°), 24.3° (±0.1°) and 27.1° (0.1°) 2θ.

6. A compound of formula (I) as claimed in claim 1 characterised by a differential scanning calorimetry curve to have an onset of melting which is in the range of 136-139° C.

7. A compound of formula (I) as claimed in claim 1 characterised by an X-ray powder diffraction pattern containing specific peaks at 5.6° (±0.1°), 12.5° (±0.1°), 14.0° (±0.1°), 17.4° (±0.1°), 18.4° (±0.1°), 21.4° (±0.1°), 22.2° (±0.1°), 22.9° (±0.1°), 24.1° (±0.1°) and 24.5° (±0.1°) 2θ.

8. A compound of formula (I) as claimed in claim 1 characterised by a differential scanning calorimetry curve to have an onset of melting which is in the range 127-132° C.

9. A compound of formula (I) as claimed in claim 1 characterised by an X-ray powder diffraction pattern containing specific peaks at 4.9° (±0.1°), 6.0° (±0.1°), 9.2° (±0.1°), 11.6° (±0.1°), 12.8° (±0.1°), 15.6° (±0.1°), 16.4° (±0.1°), 17.2° (±0.1°) and 18.1° (±0.1°) 2θ.

10. A compound of formula (I) as claimed in claim 1 characterised by a differential scanning calorimetry curve to have an onset of melting which at approximately 139° C.

11. A process for the preparation of a compound as claimed in claim 1, comprising crystallizing a compound of formula (I) from a solvent selected from the group consisting of a lower alkyl acetate, a lower alkyl alcohol, an aliphatic hydrocarbon, an aromatic hydrocarbon, a dialkyl ether, a dialkyl ketone, acetonitrile, water, and a mixture thereof.

12. A process as claimed in claim 11, wherein the solvent in selected from the group consisting of ethanol, ethyl acetate, iso-propanol, iso-octane, acetonitrile, water, and a mixture thereof.

13. A process as claimed in claim 12 wherein the solvent is selected from the group consisting of a mixture of methanol and water, ethanol, ethyl acetate, a mixture of ethanol and water, a mixture of iso-propanol and water, a mixture of ethyl acetate and iso-octane, and acetonitrile.

14. A process for the production of a compound of formula (I) as claimed in claim 1, characterised by an X-ray powder diffraction pattern containing specific peaks at 5.3° (±0.1°), 20.1° (±0.1°), 20.7° (±0.1°), 21.0° (±0.1°) and 21.3° (±0.1°) 2θ, comprising crystallizing the compound of formula (I) from a mixture of methanol and water.

15. A process as claimed in claim 14 which includes the step of using a seed.

16. A process according to claim 15 in which the seed is prepared by melting a compound of formula (I):

characterised by an X-ray powder diffraction pattern containing specific peaks of high intensity at 5.3° (±0.1°), 8.0° (0.1°), 9.6° (±0.1°), 13.9° (±0.1°), 15.3° (±0.1°), 20.1° (±0.1°), 20.7° (±0.1°), 21.0° (±0.1°), 21.3° (±0.1°), 26.2° (±0.1°) and 27.5° (±0.1°) 2θ.

17. A process for the production of a compound of formula (I) as claimed in claim 1, characterised by an X-ray powder diffraction pattern containing specific peaks of high intensity at 14.0° (±0.1°), 17.4° (±0.1°), 18.4° (±0.1°), 21.4° (±0.1°) and 24.1° (±0.1°) 2θ, comprising crystallizing the compound of formula (I) from an alcohol.

18. A process for the production of a compound of formula (I) as claimed in claim 1, characterised by an X-ray powder diffraction pattern containing specific peaks of high intensity at 5.5° (±0.1°), 13.5° (±0.1°), 18.3° (±0.1°), 22.7° (±0.1°) and 24.3°(±0.1°) 2θ, comprising crystallizing the compound of formula (I) from a solvent selected from the group consisting of ethyl acetate and chloroform.

19. A process for the production of a compound of formula (I) as claimed in claim 1, characterised by an X-ray powder diffraction pattern containing specific peaks of high intensity at 14.0° (±0.1°), 17.4°(±0.1°), 18.4° (±0.1°), 21.4° (±0.1°) and 24.1°(±0.1°) 2θ, comprising slurrying a compound of formula (I) in an IPA/water solvent system at a temperature of 5 to 65° C.

20. A process for the production of a compound of formula (I) as claimed in claim 1, characterised by an X-ray powder diffraction pattern containing specific peaks of high intensity at 4.9° (±0.1°), 9.2° (±0.1°), 11.6° (±0.1°), 15.6° (±0.1°) and 16.4° (±0.1°) 2θ, comprising crystallizing the compound of formula (I) from acetonitrile.

21. A pharmaceutical composition comprising a compound as claimed in claim 1 in admixture with a pharmaceutically acceptable adjuvant, diluent or carrier.

22. A method of treatment of arterial thrombotic complications selected from the group consisting of unstable angina, thrombotic or embolic stroke, transient ischaemic attacks, peripheral vascular disease and myocardial infarction in patients with coronary artery, cerebrovascular or peripheral vascular disease, which comprises administering to a person suffering from such a disorder a therapeutically effective amount of a compound as claimed in claim 1.

23. A method of treatment of arterial thrombotic complications selected from the group consisting of unstable angina, thrombotic or embolic stroke, transient ischaemic attacks, peripheral vascular disease and myocardial infarction in patients with coronary artery, cerebrovascular or peripheral vascular disease, which comprises administering to a person suffering from such a disorder a therapeutically effective amount of a compound as claimed in claim 3.

24. A method of treatment of arterial thrombotic complications selected from the group consisting of unstable angina, thrombotic or embolic stroke, transient ischaemic attacks, peripheral vascular disease and myocardial infarction in patents with coronary artery, cerebrovascular or peripheral vascular disease, which comprises administering to a person suffering from such a disorder a therapeutically effective amount of a compound as claimed in claim 5.

25. A method of treatment of arterial thrombotic complications selected from the group consisting of unstable angina, thrombotic or embolic stroke, transient ischaemic attacks, peripheral vascular disease and myocardial infarction in patients with coronary artery, cerebrovascular or peripheral vascular disease, which comprises administering to a person suffering from such a disorder a therapeutically effective amount of a compound as claimed in claim 7.

26. A method of treatment of arterial thrombotic complications selected from the group consisting of unstable angina, thrombotic or embolic stroke, transient ischaemic attacks, peripheral vascular disease and myocardial infarction in patients with coronary artery, cerebrovascular or peripheral vascular disease, which comprises administering to a person suffering from such a disorder a therapeutically effective amount of a compound as claimed in claim 9.

27. A method of treatment of an arterial thrombotic complication in a patient with coronary artery, cerebrovascular or peripheral vascular disease, which comprises administering to a person suffering from such a disorder a therapeutically effective amount of a compound as claimed in claim 1, wherein the arterial thrombotic complication is an arterial complication due to angioplasty, endarterectomy, stent placement, vascular graft surgery and thrombotic complications of surgical or mechanical damage.

28. A method of treatment of an arterial thrombotic complication in a patient with coronary artery, cerebrovascular or peripheral vascular disease, which comprises administering to a person suffering from such a disorder a therapeutically effective amount of a compound as claimed in claim 3, wherein the arterial thrombotic complication is an arterial complication due to angioplasty, endarterectomy, stent placement, vascular graft surgery and thrombotic complications of surgical or mechanical damage.

29. A method of treatment of an arterial thrombotic complication in a patient with coronary artery, cerebrovascular or peripheral vascular disease, which comprises administering to a person suffering from such a disorder a therapeutically effective amount of a compound as claimed in claim 5, wherein the arterial thrombotic complication is an arterial complication due to angioplasty, endarterectomy, stent placement, vascular graft surgery and thrombotic complications of surgical or mechanical damage.

30. A method of treatment of an arterial thrombotic complication in a patient with coronary artery, cerebrovascular or peripheral vascular disease, which comprises administering to a person suffering from such a disorder a therapeutically effective amount of a compound as claimed in claim 7, wherein the arterial thrombotic complication is an arterial complication due to angioplasty, endarterectomy, stent placement, vascular graft surgery and thrombotic complications of surgical or mechanical damage.

31. A method of treatment of an arterial thrombotic complication in a patient with coronary artery, cerebrovascular or peripheral vascular disease, which comprises administering to a person suffering from such a disorder a therapeutically effective amount of a compound as claimed in claim 9, wherein the arterial thrombotic complication is an arterial complication due to angioplasty, endarterectomy, stent placement, vascular graft surgery and thrombotic complications of surgical or mechanical damage.

* * * * *